(12) United States Patent
Khursheed

(10) Patent No.: US 6,906,335 B2
(45) Date of Patent: Jun. 14, 2005

(54) LENS FOR A SCANNING ELECTRON MICROSCOPE

(75) Inventor: Anjam Khursheed, Singapore (SG)

(73) Assignee: National University of Singapore, Singapore (SG)

( * ) Notice: Subject to any disclaimer, the term of this patent is extended or adjusted under 35 U.S.C. 154(b) by 175 days.

(21) Appl. No.: 10/275,203

(22) PCT Filed: May 2, 2001

(86) PCT No.: PCT/SG01/00083

§ 371 (c)(1),
(2), (4) Date: Jan. 8, 2003

(87) PCT Pub. No.: WO01/84593

PCT Pub. Date: Nov. 8, 2001

(65) Prior Publication Data

US 2004/0084620 A1 May 6, 2004

(30) Foreign Application Priority Data

May 4, 2000 (SG) .......................... 200002421

(51) Int. Cl.⁷ .............................................. H01J 37/18
(52) U.S. Cl. ................................................ 250/442.11
(58) Field of Search ......................... 250/442.1, 396 R, 250/397, 396 ML, 310, 311, 440.11, 441.11, 442.11

(56) References Cited

U.S. PATENT DOCUMENTS 4,866,280 A * 9/1989 Ohtaka .................. 250/442.11
5,371,371 A * 12/1994 Yamazaki et al. ...... 250/396 R
5,981,947 A * 11/1999 Nakasuji et al. ............ 250/310

FOREIGN PATENT DOCUMENTS

| JP | 58115383 | 9/1983 |
| JP | 63 224137 A | 9/1988 |
| JP | 06176729 | 6/1994 |

OTHER PUBLICATIONS

Pawley, J.B., "Practical Aspects of High–Resolution LVSEM," *Scanning*, vol. 12, P247–252, 1990.
Reimer, L., *Scanning Electron Microscopy, Physics of Image Formation and Microanalysis*, Spinger, 2nd Edition, 1998, P27, Section 2.2.3.
JSM–6000F, JEOL, 1–2 Musashino 3–Chroms, Akishima Tokyo 196.
Hitachi S–5000, Hitachi Japan.

* cited by examiner

Primary Examiner—John R. Lee
Assistant Examiner—Paul M. Gurzo
(74) Attorney, Agent, or Firm—David Jaffer; Pillsbury Winthrop LLP

(57) ABSTRACT

A lens (15) for a scanning electron microscope is adapted to be removably mounted on a specimen stage (1). The lens (15) includes a magnetic circuit (2, 3, 4, 7) having a first magnetic pole piece (7) and a second magnetic pole piece (4), and a specimen holder (5). The specimen holder (5) is located between the first and second magnetic pole pieces (4, 7). The magnetic circuit (2, 3, 4, 7) also includes a lens bore (18) to permit an electron beam (9) to strike a surface of a specimen mounted on the specimen holder (5), in use. The lens bore (18) has a width of greater than 1 mm.

7 Claims, 2 Drawing Sheets

Figure 1:
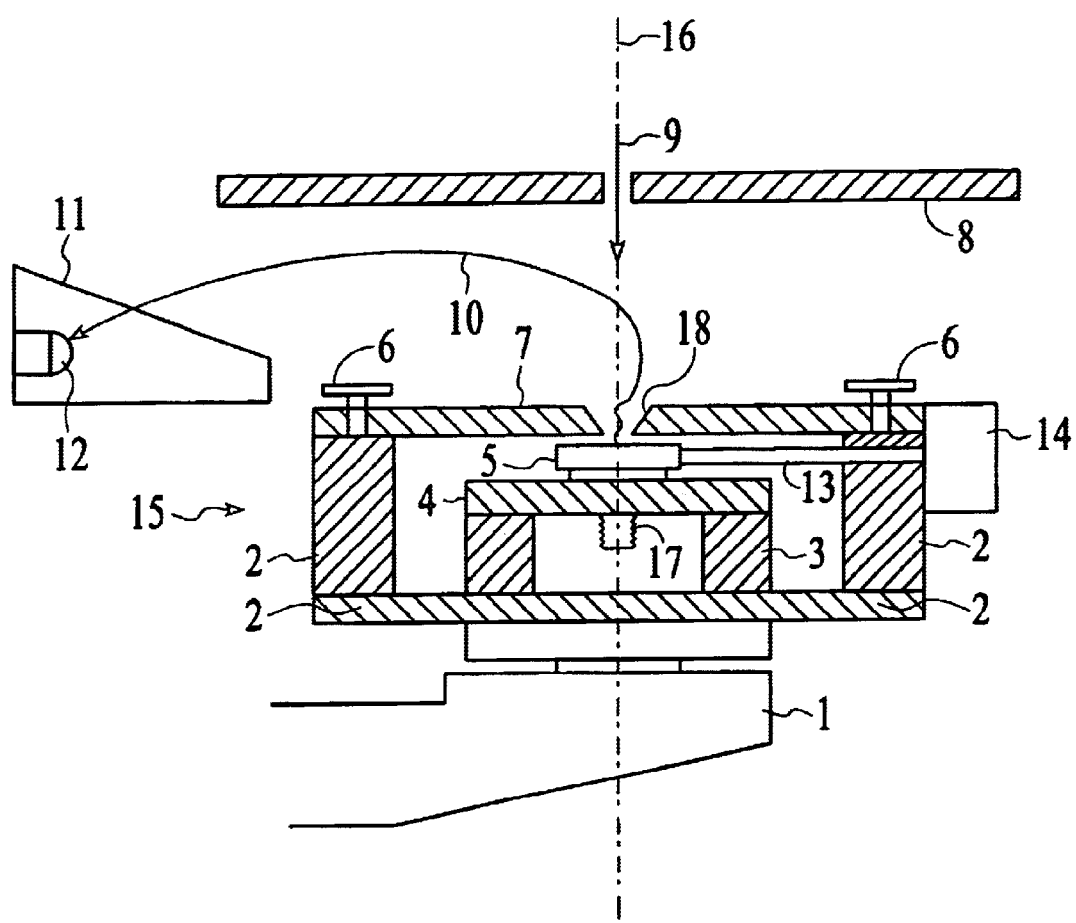

Conventional Image
(Magnification of 70,000)

Image with Add-on lens

LENS FOR A SCANNING ELECTRON MICROSCOPE

This application is the National Phase of International Application PCT/SG01/00083 filed 2 May 2001 which designated the U.S. and that International Application was published under PCT Article 21(2) in English.

In most scanning electron microscopes (SEMs), the specimen is placed in a field free region some 5 to 20 mm below the objective lens. This distance, known as the working distance, limits the SEM's spatial resolution. For optimum performance, the specimen should be placed in the lens gap, at the axial field peak, but this is impractical since in most SEMs, the scintillator and backscattered detectors are situated below the objective lens, and there is usually no access to the space inside the lens or above it. The type of lenses which place the specimen in the magnetic gap are known as "in-lens" or "immersion" objective lenses, and they typically improve the spatial resolution of scanning electron microscopes by a factor of three [L. Reimer, Scanning Electron Microscopy, Physics of image formation and microanalysis, Spinger, $2^{nd}$ edition, 1998, p27, section 2.2.3]. As a specimen in-lens arrangement significantly improves the SEM performance, several SEMs have been specially designed to function in this way [JSM6000F, JEOL, 1-2 Musashino 3-chroms, Akishima, Tokyo 196, and, Hitachi S-5000, Hitachi, Japan, see also J. B. Pawley, "Practical aspects of high-resolution LVSEM", Scanning, Vol. 12, p247–252, 1990].

However, these systems are relatively expensive and have not grown in popularity. This is in part due to their restriction on the specimen thickness (limited to less than 3 mm).

In accordance with the present invention, there is provided a lens for a scanning electron microscope, the lens being adapted to be removably mounted on a specimen stage of a scanning electron microscope, the lens comprising a magnetic circuit comprising a first magnetic pole piece and a second magnetic pole piece, a specimen holder, the specimen holder being located between the first and second magnetic pole pieces, and a lens bore to permit an electron beam to strike a surface of a specimen mounted on the specimen holder, in use, and wherein the lens bore has a width of greater than 1 mm.

Typically, the lens bore has a width of at least 2 mm, preferably has a width of from 2 mm to 10 mm, and most preferably has a width of 4 mm.

Preferably, the lens bore is in one of the first and second magnetic pole pieces.

Typically, the lens bore is circular.

Preferably, the magnetic circuit comprises a permanent magnetic. Typically, the permanent magnet has a strength of approximately $0.9 \times 10^6$ $Am^{-1}$.

However, it is possible that the magnetic circuit may comprise an electro-magnet.

Preferably, the specimen holder is movably located between the first and second magnetic pole pieces for movement in a direction substantially parallel to the magnetic field between the first and second magnetic pole pieces. This has the advantage of permitting the working distance to be varied to optimise the resolution. Typically, the specimen holder is movably mounted on the other of the first and second magnetic pole pieces, where the lens bore is in the one of the first and second magnetic pole pieces.

Typically, the device further comprises a movement mechanism to permit lateral movement of the specimen holder.

Figure 2A:
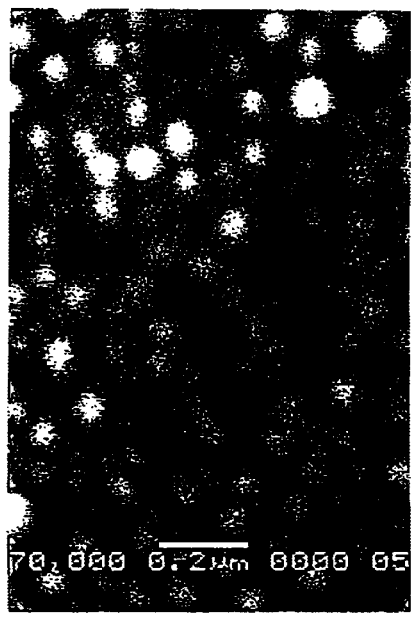
Figure 2B:
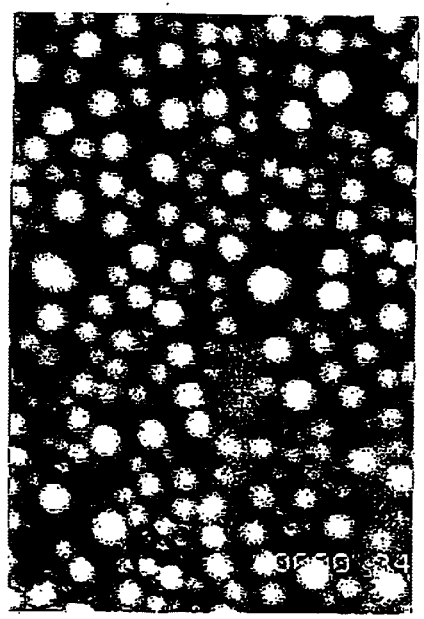

An example of a specimen mounting device in accordance with the invention will now be described with reference to the accompanying drawings, in which:

FIG. 1 is a cross-sectional view of an in-lens attachment for a scanning electron microscope; and FIGS. 2a and 2b show an image of a specimen from a scanning electron microscope without and with the attachment, respectively.

FIG. 1 is a schematic cross-sectional view of an in-lens attachment 15 located inside an SEM specimen chamber. The cross-sectional view is on a plane that is coincident with an optical axis 16 of the SEM. The in-lens attachment 15 is located on a specimen stage 1 of the SEM. The in-lens attachment comprises a permanent magnet 3, in the form of a cylindrical ring tube, and is magnetised in a direction parallel to the SEM optical axis 16. It is also possible to use a tube magnet, rather than the ring geometry indicated in FIG. 1. The magnet 3 has a strength of approximately $0.9 \times 10^6$ $Am^{-1}$ which provides a peak magnetic field of approximately 0.287 T. The magnet 3 forms part of a magnetic circuit which also consists of a surrounding cylindrical block 2, a first magnetic pole piece (or upper pole piece) in the form of a top plate 7, and a second magnetic pole piece (or lower pole piece) in the form of an intermediate plate 4. The plates 4, 7 effectively form the pole pieces of the magnetic circuit. The separation of the plates 4 and 7 defines the magnetic gap size, and typically ranges from 5 mm to 15 mm. A specimen holder 5 is mounted on the plate 4 and a specimen-(not shown) may be inserted into the specimen holder 5 so that the specimen surface lies within a few millimetres of the lens top plate 7. The separation of the specimen surface and the top plate 7 defines the "working distance". The specimen holder 5 is made from non-magnetic material such as aluminium and is mounted to the intermediate plate 4 by an adjusting screw 17. The adjusting screw 17 permits the working distance to be adjusted.

The plate 7 has a lens bore 18 which permits a primary beam 9 of the SEM to pass through the top plate 7 and strike the specimen surface. The diameter of the bore 18 is dependent to some extent on the working distance but should generally be greater than 1 mm, typically at least 2 mm, and preferably at least 4 mm, in order to obtain sufficient resolution of the final image from the SEM.

Screws 6 in the top plate 7 permit removal of the top plate 7 to allow insertion of the specimen into the specimen holder 5. The specimen holder 5 can be moved in the x and y directions by two spindles 13 (only one shown) orientated at right angles to each other and to the optical axis 16. Each spindle 13 is coupled to an electric motor 14 (only one shown), located on the side of the attachment 15, which drives the respective spindle to move the specimen holder in the desired direction. Electrical wires (not shown in FIG. 1) connect the motors 14 with a power supply located outside the SEM. In this way, specimen movement can be controlled from outside the SEM.

The total height of the attachment 15, comprising of the top plate 7 and the block 2, is typically less than 34 mm. The distance from the top plate 7 to the pole-piece of the SEM final lens 8, typically ranges from 20 to 30 mm, and depends on the specific layout of the SEM in which the attachment is used.

In use, a specimen is placed in the specimen holder 5, the holder 5 placed on the adjustable mounting plate 19 and the plate 7 attached by screws 6. The attachment 15 is then placed on a specimen stage 1 of a conventional SEM. The primary beam 9 travels through the bore 18 in the top plate 7 and strikes the specimen in the holder 5. Secondary electrons 10 that leave the specimen are collimated by the strongly decreasing field gradient, and spiral up through the bore 18. Some of the secondary electrons 10 are attracted to a scintillator cage 11 on the SEM and collected by a scintillator detector 12 located within the cage 11. Focussing of the primary beam 9 onto the specimen is performed using the conventional SEM objective lens, and so it is possible to use a permanent magnet 3. However, it is possible that this could be replaced by an electro-magnet.

FIG. 2a shows an image of a tin-on-carbon specimen obtained using a JEOL 5600 tungsten gun SEM without use of the attachment 15. A 5 keV primary beam 9 was used with a working distance of 5 mm and a magnification of 70,000.

FIG. 2b shows an image of the same specimen obtained using the same JEOL 5600 tungsten gun SEM but using the attachment 15, the primary beam 9 and the magnification were the same as for FIG. 2a. Comparison of these images demonstrates that the attachment improves the spatial resolution performance by around a factor of three: the minimum feature separation is approximately 20 nm without the lens, and around 7 nm with the lens There are several factors in the design of the add-on lens invention which are important to its ability to improve the resolution of existing SEMs. The size of the central hole in the lens top plate must be large enough so that deflection aberrations do not significantly degrade the image resolution. Also, a small hole will make the focal length very short and make it difficult to focus the image by the normal method of adjusting the SEM's objective lens current. Experimental results showed that a hole diameter of 4 mm or greater gave good results.

Another important element in the correct functioning of the add-on lens unit is choosing the correct working distance. For a given primary beam voltage, the working distance must be varied in order to produce high resolution images. In general, as the primary beam's voltage is reduced, the lens working distance must also be decreased, that is, the specimen surface must be brought closer to the top plate 7. This highlights the importance of being able to adjust the height of the specimen holder.

What is claimed is:

1. An add-on lens for use with a scanning electron microscope, the lens being adapted to be removably mounted on a specimen stage of and below an objective lens of the scanning electron microscope, the add-on lens including (a) a magnetic circuit using a permanent magnet and having a first magnetic pole piece and a second magnetic pole piece, (b) a specimen holder, the specimen holder movably mounted between the first and second magnetic pole pieces for movement in a direction substantially parallel to the magnetic field between the first and second magnetic pole pieces, and (c) a lens bore to permit an electron beam to strike a surface of a specimen mounted on the specimen holder, wherein the lens bore has a width of greater than 1 mm.

2. A lens according to claim 1, wherein the lens bore has a width of at least 2 mm.

3. A lens according to claim 2, wherein the lens bore has a width of from 2 mm to 10 mm.

4. A lens according to claim 3, wherein the lens bore has a width of 4 mm.

5. A lens according to claim 1, wherein the lens bore is in one of the first and second magnetic pole pieces.

6. A lens according to claim 5, wherein the specimen holder is movably mounted on the other of the first and second magnetic pole pieces.

7. A lens according to claim 1, wherein the specimen holder is movably mounted between the first and second magnetic pole pieces for movement in a direction transverse to the magnetic field between the first and second magnetic pole pieces.

* * * * *